US006283924B1

(12) United States Patent
Ouchi

(10) Patent No.: US 6,283,924 B1
(45) Date of Patent: Sep. 4, 2001

(54) ENDOSCOPIC BIOPSY FORCEPS

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/441,507

(22) Filed: Nov. 17, 1999

(30) Foreign Application Priority Data

Nov. 20, 1998 (JP) ..................... 10-330360
Oct. 15, 1999 (JP) ..................... 11-293474

(51) Int. Cl.$^{7}$ ..................... A61B 10/00
(52) U.S. Cl. ..................... 600/564
(58) Field of Search ..................... 600/564, 562, 600/104, 300, 101

(56) References Cited

U.S. PATENT DOCUMENTS 5,383,471 * 1/1995 Funnell ..................... 600/564
5,386,817 * 2/1995 Jones ..................... 600/104

FOREIGN PATENT DOCUMENTS 1-54059 11/1989 (JP) .
3-26608 4/1991 (JP) .
5-39684 10/1993 (JP) .
6-16789 3/1994 (JP) .

* cited by examiner

*Primary Examiner*—Eric F. Winakur
*Assistant Examiner*—Brian Szmal
(74) *Attorney, Agent, or Firm*—Greenblum & Berstein, P.L.C.

(57) ABSTRACT

Endoscopic biopsy forceps with which the tissue to be analyzed by biopsy can be severed positively to the last bit so that a specimen of the tissue can be collected with minimum occurrence of bleeding. The opposed open ends of two forceps cups are made slightly different in size so that when the two forceps cups are closed, the open end of one forceps cup rests into the open end of the other forceps cup.

10 Claims, 4 Drawing Sheets

12 II 14 13 1 12a 11a 11 II 2 10

1
2
13
14
10
II
II
12
11
11a
12a 20
1
10
12
11

ENDOSCOPIC BIOPSY FORCEPS

BACKGROUND OF THE INVENTION

The present invention relates to endoscopic biopsy forceps that is passed into a forceps channel in an endoscope to collect a tissue specimen to be analyzed by biopsy.

Endoscopic biopsy forceps generally comprise a sheath that is inserted into or removed out of a forceps channel in an endoscope, a manipulating wire provided to extend through the sheath and a pair of forceps cups that are provided at the distal end of the sheath and which are driven to open or close like beaks by advancing or retracting the manipulating wire in the axial direction. The forceps cups are formed in substantially symmetrical shapes and their opposed open ends have sharp blade-like edges.

To collect a tissue to be analyzed by biopsy, the operator pulls the manipulating wire toward himself so that the forceps cups are closed, whereupon tissue severing edges at the open ends of the forceps cups sever the tissue and the desired tissue specimen is collected in the forceps cups.

When the tissue pinched between the forceps cups is being severed, the forceps cups receive an irregular strong force, and a lateral displacement or a tilt, although small in amount, will occur in the forceps cups as they move like beaks.

As a result, even when the two forceps cups are completely closed, heir tissue severing edges do not meet perfectly but often fail to sever the tissue neatly to the last bit.

To deal with this case, the operator frequently tears off the tissue by pulling the biopsy forceps toward himself as it is pinched between the forceps cups but then the mucosa of the patient is damaged to cause undue bleeding.

SUMMARY OF THE INVENTION

An object, therefore, of the present invention is to provide endoscopic biopsy forceps with which the tissue to be analyzed by biopsy can be severed positively to the last bit so that a specimen of the tissue can be collected with minimum occurrence of bleeding.

To achieve the above-noted object, the present invention provides a novel arrangement for endoscopic biopsy forceps, in which forceps cups has opposed open ends slightly different in size, so that when said forceps cups are closed, the open end of one forceps cup rests into the open end of the other forceps cup.

The present invention further provides a novel arrangement for endoscopic biopsy forceps, in which forceps cups has opposed open ends and tissue severing edges which are formed on the open ends and slightly different in size, so that when said forceps cups are closed, the tissue severing edge of one forceps cup rests into the tissue severing edge of the other forceps cup.

In accordance with the present invention, when a tissue pinched between two forceps cups is being severed, the cups engage each other such that a tissue severing edge of the smaller cup is guided to rest inward of the tissue severing edge of the larger cup. As a result, the tissue can be severed positively to the last bit so that the desired specimen of the tissue is collected with minimum occurrence of bleeding.

The present disclosure relates to the subject matter contained in Japanese patent application Nos. Hei. 10-330360 (filed on Nov. 20, 1998) and Hei. 11-293474 (filed on Oct. 15, 1999), which are expressly incorporated herein by reference in their entireties.

DESCRIPTION OF THE PREFERRED EMBODIMENTS

Preferred embodiments of the invention will be described below with reference to the accompanying drawings.

Figure 5:
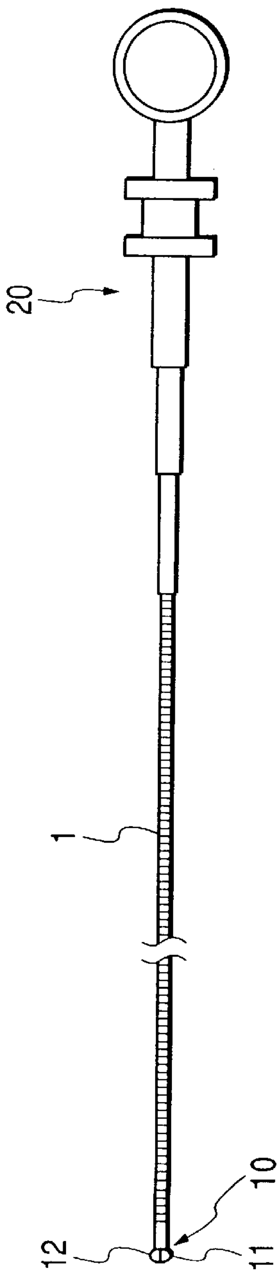
FIG. 5 is a side view of the same endoscopic biopsy forceps.

FIG. 5 shows the endoscopic biopsy forceps of the invention. The endoscopic biopsy forceps has a flexible sheath 1 that is to be inserted into or removed out of a forceps channel in an endoscope (not shown) and which typically comprises a closely wound coil pipe. The flexible sheath 1 has a manipulating wire provided to extend through it over the entire length such that the wire is capable of moving back and forth along the axis of the sheath 1. A closely wound coil pipe is not the sole example of the sheath 1; the sheath 1 may be constructed by a closely wound coil pipe covered with a flexible tube, or any other suitable construction may be employed.

The basal end of the sheath 1 (which is closer to the operator) is coupled to a manipulating portion 20 for moving the manipulating wire back and forth. The distal end of the sheath 1 is coupled to a tip activating portion 10 that is driven with the manipulating wire.

Figure 1:
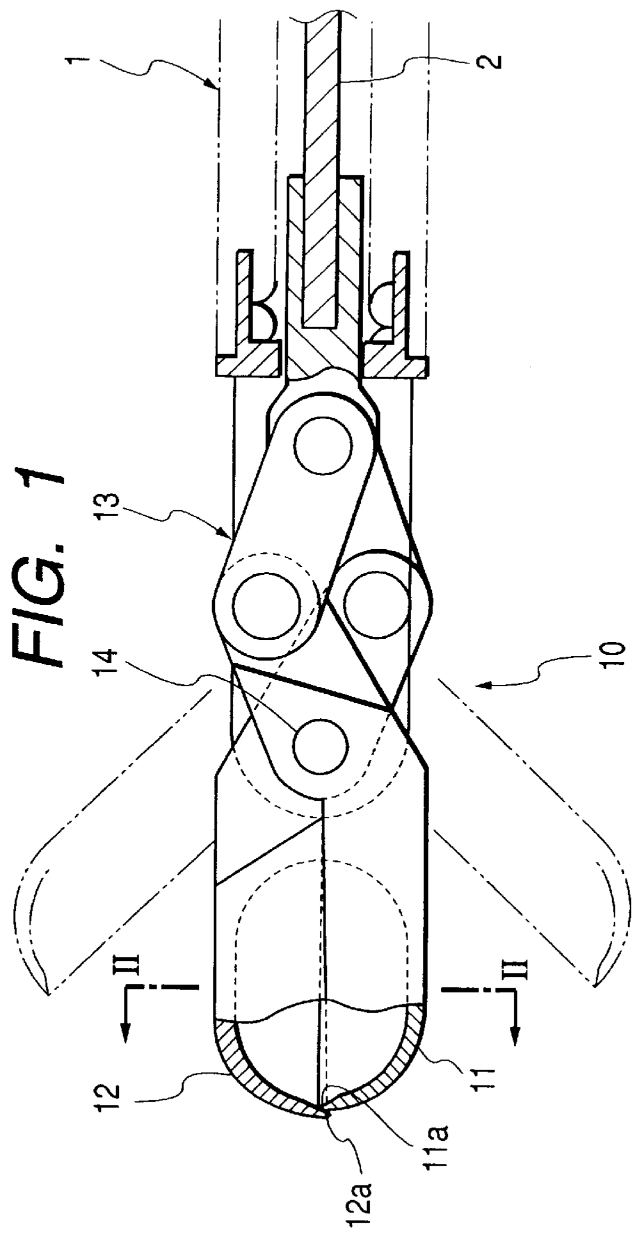
FIG. 1 is a longitudinal section of the distal end portion of endoscopic biopsy forceps according to an embodiment of the invention.

FIG. 1 shows the tip activating portion 10 which comprises a link mechanism 13 of a known construction that is driven with the manipulating wire 2, and a pair of forceps cups 11 and 12 that are adapted to pivot about a support shaft 14 so that they open or close like beaks. When they open, the forceps cups 11 and 12 come to the positions indicated by the two-dotted chain line.

The open ends of the two forceps cups 11 and 12 are shaped to have oblong cross sections that face each other when the two cups are closed. Those open ends have sharp edges 11*a* and 12*a* for severing a tissue.

The open ends of the forceps cups 11 and 12 are almost symmetrical in shape but slightly different in size such that when they are closed, the peripheral or edge portion of the open end of the first forceps cup 11 is in contact with a slope of the open end of the second forceps cup 12 so that the tissue severing edge 11*a* of the first forceps cup 11 rests inward of the tissue severing edge 12*a* of the second forceps cup 12.

Figure 2:
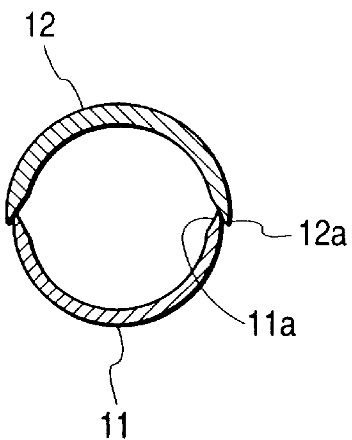
FIG. 2 is section II—II of FIG. 1 or a cross section of the distal end portion of the same endoscopic biopsy forceps.

This relationship holds not only in the longitudinal direction but also in the circumferential direction; as shown in FIG. 2 which is section II—II of FIG. 1, the tissue severing edges 11*a* of the first forceps cup 11 rest inward of the tissue severing edges 12*a* of the second forceps cup 12 over the whole peripheries of the first and second forceps cups 11 and 12.

The endoscopic biopsy forceps having the construction described above is used in the following way. With the forceps cups 11 and 12 closed, the sheath 1 is inserted into the forceps channel of an endoscope (not shown). When a diseased part is detected, the cups are opened and pressed onto it. Thereafter, the manipulating wire 2 is pulled to close the cups, whereupon the tissue severing edges 11*a* and 12*a* of the cups sever the tissue of the diseased part.

Figure 3:
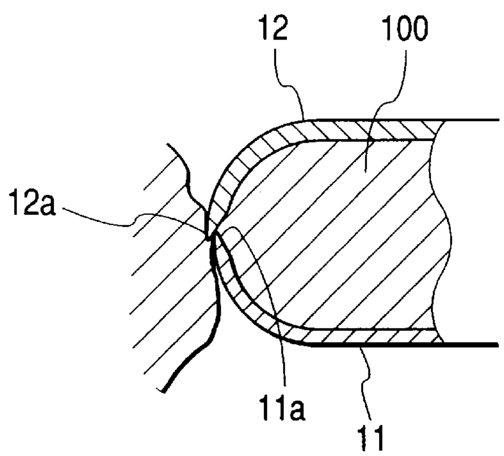
FIG. 3 is a longitudinal section of the distal end portion of the same endoscopic biopsy forceps as it is used in practice.
Figure 4:
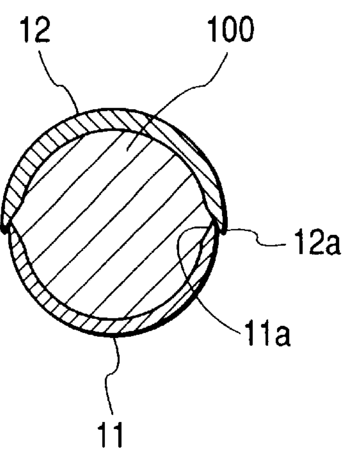
FIG. 4 is a cross section of the distal end portion of the same endoscopic biopsy forceps as it is used in practice.

When the two forceps cups 11 and 12 are completely closed, the tissue severing edge 11*a* of the first cup 11 rests inward of the tissue severing edge 12*a* of the second cup 12 as shown in FIGS. 3 and 4 which are a longitudinal and a cross section, respectively, of the cups.

When the tissue pinched between the two cups is being severed, an irregular strong force acts on the cups to develop a lateral displacement or a tilt. In the present invention, the two forceps cups engage each other such that the tissue severing edge 11*a* of the smaller cup 11 is guided to rest inward of the tissue severing edge 12*a* of the larger cup 12; as a result, a shear action occurs between those tissue severing edges 11*a* and 12*a*, and the tissue to be analyzed by biopsy is severed neatly to the last bit so that the desired specimen of the tissue 100 is collected within the closed cups.

Therefore, no part of the tissue is forcibly pulled or torn off and the mucosa of the patient is not damaged to cause undue bleeding. What is more, the tissue severing edges 11*a* and 12*a* of the forceps cups 11 and 12 do not bump each other, so they stand up to prolonged use without nicking or wear.

Note that the present invention should not be limited to the embodiment described above, and can be modified in various ways.

For example, the pair of forceps cups 11 and 12 can be formed into various mutual configuration.

Figure 6:
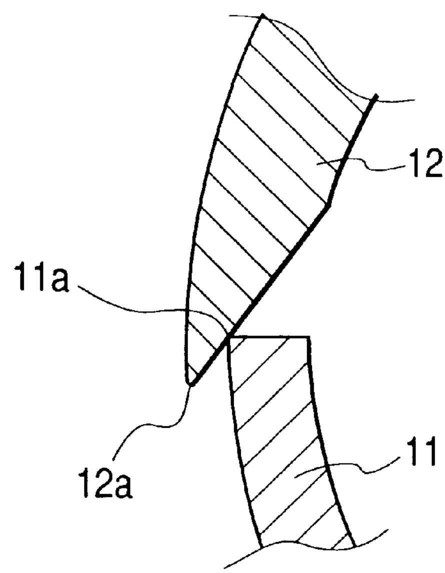
FIG. 6 is an enlarged longitudinal section showing a state that forceps cups according to a second embodiment are closed completely.
Figure 7:
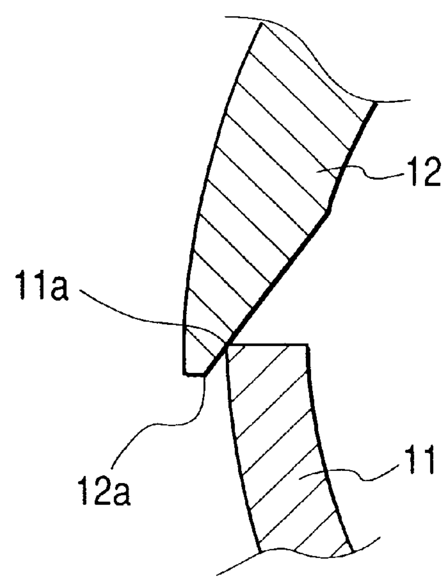
FIG. 7 is an enlarged longitudinal section showing a state that forceps cups according to a third embodiment are closed completely.
Figure 8:
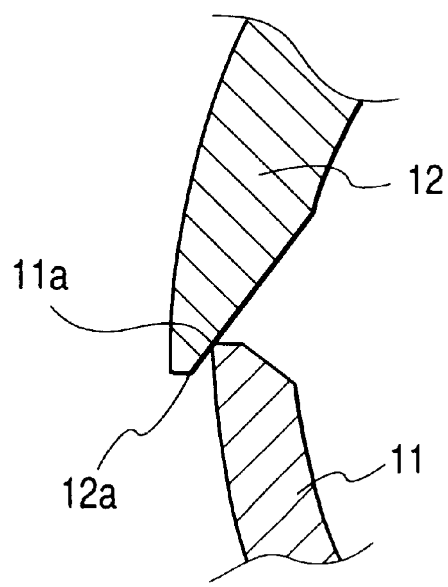
FIG. 8 is an enlarged longitudinal section showing a state that forceps cups according to a fourth embodiment are closed completely.

For example, as shown in FIGS. 6 to 8, one or both of the open ends of the forceps cup 11 and 12 may be planar, may have a small planar surface contiguous to the distal end of a slope, etc.

In each of the embodiments as well, when the pair of forceps cups are closed, the peripheral portion of the open end of the first forceps cup 11 is in contact with the slope of the open end of the second forceps cup 12.

Figure 9:
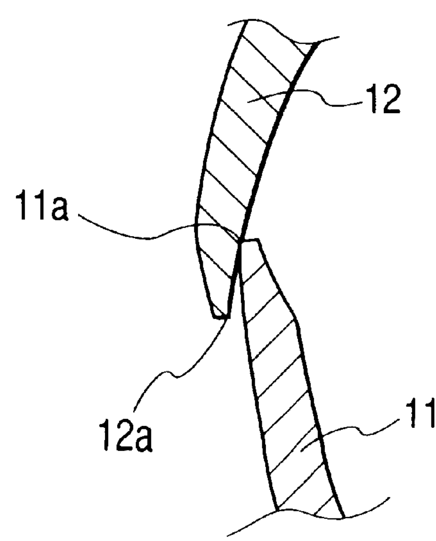
FIG. 9 is an enlarged longitudinal section showing a state that forceps cups according to a fifth embodiment are closed completely.
Figure 10:
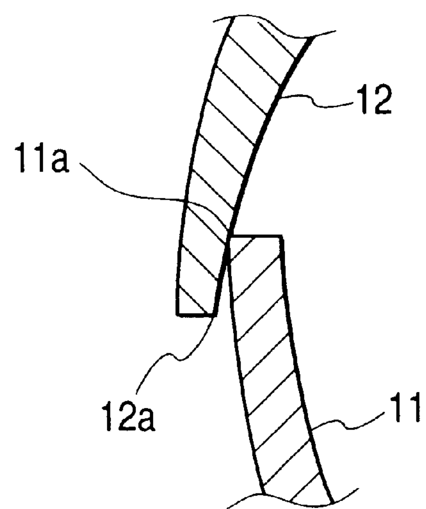
FIG. 10 is an enlarged longitudinal section showing a state that forceps cups according to a sixth embodiment are closed completely.
Figure 11:
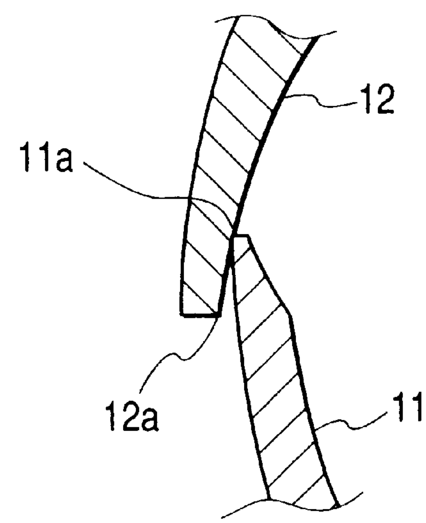
FIG. 11 is an enlarged longitudinal section showing a state that forceps cups according to a seventh embodiment are closed completely.

Further, as shown in FIGS. 9 to 11, the forceps cups 11 and 12 may be arranged such that when the pair of forceps cups 11 and 12 are being closed, the periphery of the open end of the first forceps cup 11 is slidingly contacted with the inner peripheral surface of the open end of the second forceps cup 12. Moreover, one or both of the open ends of the forceps cups 11 and 12 may be formed into a blade, a plate or a combination of them.

Figure 12:
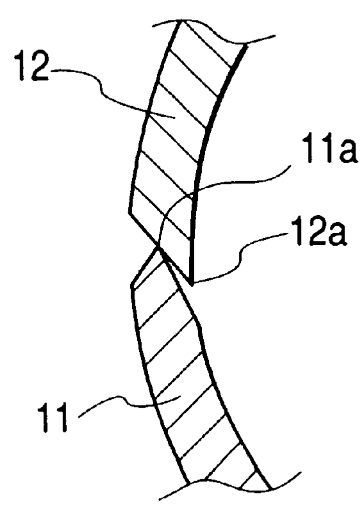
FIG. 12 is an enlarged longitudinal section showing a state that forceps cups according to an eighth embodiment are closed completely.
Figure 13:
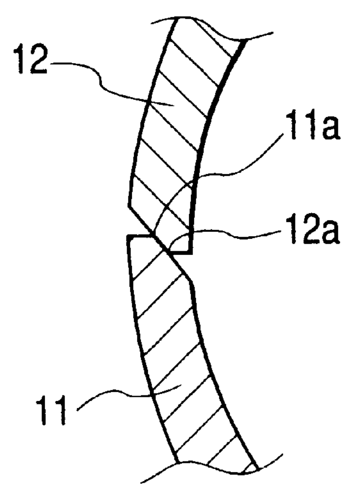
FIG. 13 is an enlarged longitudinal section showing a state that forceps cups according to a ninth embodiment are closed completely.

As shown in FIGS. 12 and 13, the pair of the forceps cups 11 and 12 may be constructed to have the tissue severing edges 11*a* and 12*a* slightly different in size from each other while the open ends of the forceps cups 11 and 12 are identical in size. In these embodiments, the tissue severing edge 12*a* of the one forceps cup 12 rests inward of the tissue severing edge 11*a* of the other forceps cup 12.

What is claimed is:

1. An endoscopic biopsy forceps, comprising:

a sheath that is at least one of insertable into and removable from a forceps channel of an endoscope;

a manipulating wire that extends through said sheath;

a pair of forceps cups provided at a distal end of said sheath and which are driven to at least one of open and close like beaks by at least one of advancing and retracting said manipulating wire in an axial direction thereof, an entire periphery of a first forceps cup, of said pair of forceps cups, forming a severing edge that slidingly contacts an inside surface of a second forceps cup, of said pair of forceps cups, so that when said pair of forceps cups are closed, a portion of a tissue sample is sharply cut by said severing edge.

2. The endoscopic biopsy forceps of claim 1, wherein said periphery of said first forceps cup contacts a slope of said second forceps cup when said pair of forceps cups are closed.

3. The endoscopic biopsy forceps of claim 2, wherein said periphery of said first forceps cup slides on a periphery of said second forceps cup when said pair of forceps cups are closed.

4. The endoscopic biopsy forceps of claim 1, wherein a tissue severing edge of said first forceps cup contacts a slope of said second forceps cup when said pair of forceps cups are closed.

5. An endoscopic biopsy forceps, comprising:

a sheath that is at least one of insertable into and removable from a forceps channel of an endoscope;

a manipulating wire that extends through said sheath;

a pair of forceps cups provided at a distal end of said sheath and which are driven to at least one of open and close like beaks by at least one of advancing and retracting said manipulating wire in an axial direction thereof, an entire periphery of a first forceps cup and a second forceps cup of said pair of forceps cups forming tissue severing edges which are slightly different in size, such that when said pair of forceps cups are closed, a tissue severing edge of said first forceps cup rests into a tissue severing edge of said second forceps cup.

6. The endoscopic biopsy forceps of claim 5, wherein said periphery of said first forceps cup contacts a slope of said second forceps cup when said pair of forceps cups are closed.

7. The endoscopic biopsy forceps of claim 6, wherein said periphery of said first forceps cup slides on a periphery of said second forceps cup when said pair of forceps cups are closed.

8. The endoscopic biopsy forceps of claim 5, wherein said tissue severing edge of said first forceps cup contacts a slope of said second forceps cup when said pair of forceps cups are closed.

9. A tip activation portion for an endoscopic forceps, comprising:

a link mechanism having a support shaft;

first forceps cup; and second forceps cup, said first forceps cup and said second forceps cup being coupled to said link mechanism and pivotable about said support shaft, each of said first forceps cup and said second forceps cup having a convex outside surface and a concave inside surface, a boundary connecting said outside surface and said inside surface presenting a cup shape, an entire periphery of said boundary forming a tissue severing edge that is brought into contact with said inside surface of said second forceps cup when said endoscopic forceps are closed.

10. A tip activation portion for an endoscopic forceps, comprising:

a link mechanism having a support shaft;

first forceps cup; and second forceps cup, said first forceps cup and said second forceps cup being coupled to said link mechanism and pivotable about said support shaft, each of said first forceps cup and said second forceps cup having a convex outside surface and a concave inside surface, a boundary connecting said outside surface and said inside surface presenting a cup shape, an entire periphery of said boundary of said first forceps cup and said second forceps cup forming a tissue severing edge, said tissue severing edge of said first forceps cup being radially offset from said tissue severing edge of said second forceps cup when said endoscopic forceps are closed.

* * * * *